US012653654B2

(12) United States Patent
Kim

(10) Patent No.: US 12,653,654 B2
(45) Date of Patent: Jun. 16, 2026

(54) ELECTRIC FIELD GENERATING DEVICE FOR ORAL CARE AND ORAL CARE DEVICE INCLUDING SAME

(71) Applicant: Proxihealthcare Inc., Ulsan (KR)

(72) Inventor: Young Wook Kim, Seoul (KR)

(73) Assignee: Proxihealthcare Inc., Ulsan (KR)

( * ) Notice: Subject to any disclaimer, the term of this patent is extended or adjusted under 35 U.S.C. 154(b) by 459 days.

(21) Appl. No.: 18/189,504

(22) Filed: Mar. 24, 2023

(65) Prior Publication Data

US 2023/0225840 A1     Jul. 20, 2023

Related U.S. Application Data

(63) Continuation of application No. PCT/KR2021/013130, filed on Sep. 27, 2021.

(30) Foreign Application Priority Data

Sep. 27, 2020     (KR) ........................ 10-2020-0125336

(51) Int. Cl.
$A61C\ 17/00$          (2006.01)
$A61C\ 19/06$          (2006.01)
$A61N\ 1/05$           (2006.01)
(52) U.S. Cl.
CPC ............ $A61C\ 17/005$ (2013.01); $A61C\ 19/06$ (2013.01); $A61N\ 1/0548$ (2013.01)
(58) Field of Classification Search
None
See application file for complete search history.

(56) References Cited

U.S. PATENT DOCUMENTS

| | | | |
|---|---|---|---|
| 2008/0199830 A1* | 8/2008 | Fontenot | A46B 13/023 |
| | | | 433/80 |
| 2013/0071807 A1* | 3/2013 | Doll | A61C 17/222 |
| | | | 433/27 |

FOREIGN PATENT DOCUMENTS

| | | | |
|---|---|---|---|
| JP | 10-080324 A | 3/1998 | |
| KR | 10-2008-0055981 A | 6/2008 | |
| KR | 10-2012-0121789 A | 11/2012 | |
| KR | 10-2014-0048326 A | 4/2014 | |
| KR | 101834665 B1 * | 3/2018 | ........... A61N 1/3603 |

OTHER PUBLICATIONS

KR-101834665-B1, Apparatus for Removing Cavity Plague, Kim 2018 (Year: 2018), Machine translation provided.*

* cited by examiner

*Primary Examiner* — Mallika D Fairchild
(74) *Attorney, Agent, or Firm* — NKL LAW; Jae Youn Kim

(57) ABSTRACT

An electric field generating device for oral care of the present invention includes: at least one electrode configured to receive a driving signal and generate an electric field corresponding to the driving signal; and a signal supply part configured to generate the driving signal by mixing an AC signal and a DC signal and supply the driving signal to an electrode.

13 Claims, 8 Drawing Sheets

ELECTRIC FIELD GENERATING DEVICE FOR ORAL CARE AND ORAL CARE DEVICE INCLUDING SAME

TECHNICAL FIELD

The present invention relates to an electric field generating device for oral care and an oral care device including the same, and more particularly, to an electric field generating device that may help oral care and an oral care device including the same.

BACKGROUND ART

Dental plaque is a sticky and transparent film that adheres to the surface of teeth. The dental plaque is formed as numerous germs (bacteria) living in the mouth adhere to certain components in saliva. The dental plaque may be formed not only on and around the teeth, but also around prostheses, braces, and dentures.

When the dental plaque in the form of a very thin and transparent film is created, the bacteria in the plaque proliferate and also increase exponentially using the sugar supplied when food is consumed. The acidic substances produced by the bacteria in the plaque dissolve the lime in the teeth, causing tooth decay, and the toxins cause inflammation in the gums.

The dental plaque itself is difficult to see with the naked eye, and it mainly occurs in deep valleys of teeth, narrow gaps between teeth, and narrow gaps between teeth and gums. Because the plaque causes problems to teeth and surrounding tissues in such a small space, it is important to remove the plaque without missing every corner, but there is a problem in that it is difficult to effectively remove such plaque using only a conventional toothbrush.

DISCLOSURE

Technical Problem

An object of the present invention to solve the above problems is to provide an electric field generating device for oral care capable of effectively removing a biofilm in the oral cavity by providing an electric field, and an oral care device including the same.

In addition, another object of the present invention is to provide an electric field generating device for oral care which amplifies oral care effects by utilizing a driving signal generated by mixing an AC signal and a DC signal, and an oral care device including the same.

Technical Solution

The electric field generating device for oral care according to an embodiment of the present invention includes at least one electrode configured to receive the driving signal and generate an electric field corresponding to the driving signal, and a signal supply part configured to mix the AC signal and the DC signal to generate the driving signal and supply the driving signal to the electrode.

In addition, the signal supply part may change at least one of the characteristics of the driving signal in response to a user's control.

In addition, the characteristics of the driving signal may include an amplitude, a frequency, and a DC offset.

In addition, the electric field generating device may include a communication part capable of wireless communication with a user's terminal, and a controller configured to transmit current characteristic information of the driving signal to the user's terminal through the communication part.

In addition, the signal supply part may change at least one of the characteristics of the driving signal in response to setting information transmitted from the user's terminal through the communication part.

In addition, the setting information may include at least one of gender, age, and periodontal disease possession information of the user.

In addition, the setting information may include at least one of an amplitude setting value, a frequency setting value, and a DC offset setting value.

In addition, the signal supply part may automatically change at least one of the characteristics of the driving signal for each unit time during a predetermined period.

In addition, the signal supply part may include a DC-DC converter configured to receive a battery voltage and converting it to output voltage, a signal generator configured to generate the AC signal using an output voltage of the DC-DC converter, a filter configured to perform a filtering operation on the AC signal generated by the signal generator, and a calibration part configured to generate the driving signal by mixing the DC signal with the AC signal supplied through the filter.

In addition, the signal supply part may further include a voltage divider configured to generate the DC signal by dividing the output voltage of the DC-DC converter.

In addition, the calibration part may include an operating amplifier.

In addition, the frequency of the driving signal may be set to 1 KHz to 1,000 MHz.

In addition, the amplitude of the driving signal may be set to 0.1 my to 3V.

In addition, the voltage value of the DC signal may be set equal to or greater than the amplitude of the AC signal.

The oral care device according to an embodiment of the present invention may comprise a head part in which at least one electrode generating an electric field in response to the driving signal is disposed, a handle part connected to the head part and having a shape capable of being gripped by a user, and a signal supply part located inside the handle part and configured to generate the driving signal by mixing the AC signal and the DC signal, and supply the driving signal to the electrode.

Advantageous Effects

According to the present invention, it is possible to provide the electric field generating device for oral care which can effectively remove a biofilm in the oral cavity through the provision of an electric field, and the oral care device including the same.

In addition, according to the present invention, it is possible to provide the electric field generating device for oral care that amplifies the oral care effect by utilizing the driving signal generated by mixing the AC signal and the DC signal, and the oral care device including the same.

DETAILED DESCRIPTION OF EXEMPLARY EMBODIMENTS

Hereinafter, embodiments of the present invention will be described in detail with reference to the accompanying drawings. However, the present invention is not limited to the embodiments disclosed below and may be implemented in various different forms. Also, it should be understood that all modifications, equivalents, or replacements thereof are included within the subject matter and scope of the present invention.

In describing elements of the present invention, terms such as first, second, A, B, (a), and (b) may be used. These terms are only used to distinguish one element from other elements, and the nature, sequence, or order of that element is not limited by the term. Further, it should be understood in this specification that if an element is described as being "connected", "combined", or "coupled" to/with any other element, the element may be directly connected, combined, or coupled to/with the other element, but another element may also be connected, combined, or coupled between both elements. In the case of being "connected", "combined", or "coupled", it may be understood as being physically or electrically connected, combined, or coupled, but is also electrically "connected", "combined", or "coupled" as needed.

Terms such as "~unit", "~er", "part", and "~module" used in this specification refer to a unit that processes at least one particular function or operation, and may be implemented with hardware, software, or a combination thereof. In addition, terms such as "comprise", "include", and "have" used in this specification denote the presence of a stated element unless the relevant context clearly indicates otherwise, and do not exclude the presence of or a possibility of addition of one or more other elements.

In this specification, the distinction between elements is only a distinction by a main function performed by each element. That is, two or more elements to be described below may be combined into one element, or one element may be divided into two or more elements according to subdivided functions. Also, each element to be described below may further perform some or all of functions performed by other elements in addition to the main function thereof, and a part of the main function of each element may be performed by other elements.

Hereinafter, with reference to drawings related to embodiments of the present invention, an oral care device according to an embodiment of the present invention will be described.

Figure 1:
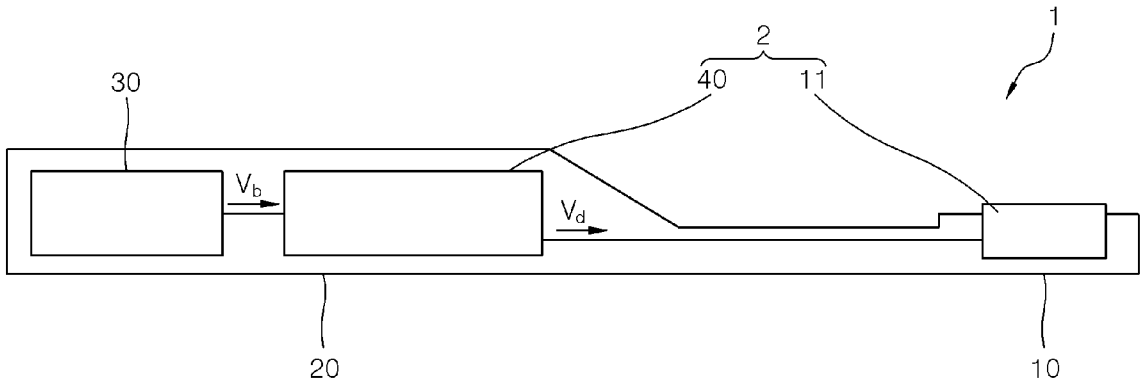
FIG. 1 is a view showing an oral care device according to an embodiment of the present invention.
Figure 2A:
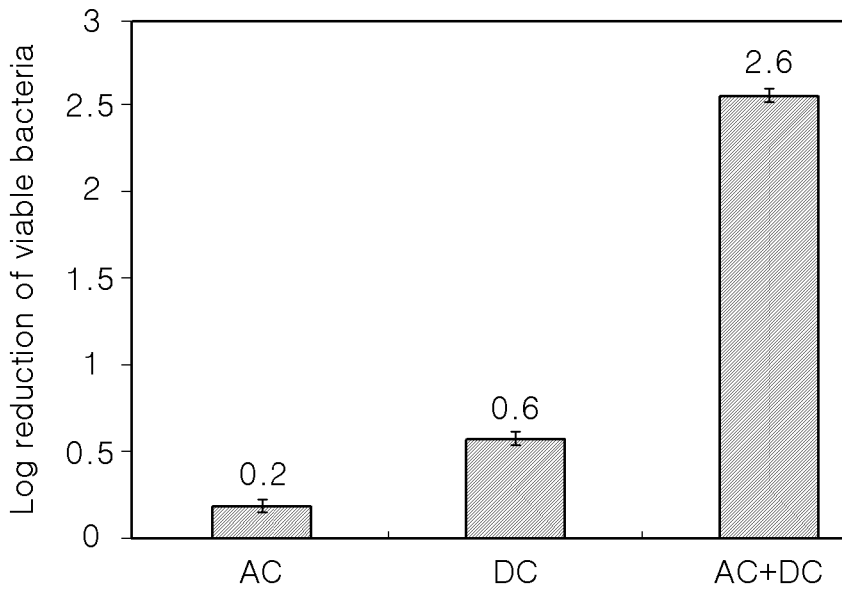
FIGS. 2A and 2B are diagrams for explaining a biofilm removal effect of the driving signal generated by mixing the AC signal and the DC signal.
Figure 2B:
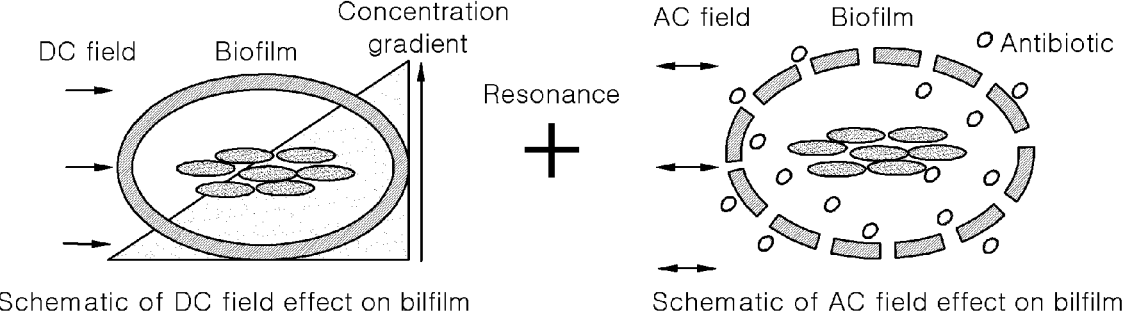

FIG. 1 is a view showing an oral care device according to an embodiment of the present invention, FIGS. 2A and 2B are diagrams for explaining a biofilm removal effect of a driving signal generated by mixing the AC signal and the DC signal.

Referring to FIG. 1, the oral care device 1 according to an embodiment of the present invention may comprise an electric field generating device 2, a head part 10, a handle part 20, and a battery 30.

The electric field generating device 2 may include at least one electrode 11 generating an electric field in response to a driving signal Vd, and a signal supply part 40 supplying the driving signal Vd to the electrode 11.

The electrode 11 may be disposed on the head part 10 and may be electrically connected to the signal supply part 40 disposed on the handle part 20 to receive the driving signal Vd.

The electrode 11 may form an electric field based on the electric energy of the driving signal Vd. Since this electric field may weaken the structure of the dental plaque, the user can effectively remove the dental plaque in the oral cavity using the oral care device 1.

In addition, the oral care device 1 may provide a microcurrent to the gums through the electrode 11 to relieve inflammation or pain in the gums.

A plurality of electrodes 11 may be disposed on the head part 10, and at least one electrode 11 among them may receive the driving signal Vd. In this case, an electrode serving as a ground electrode may be additionally installed on the head part 10.

In addition, although the electrode 11 is shown in a form protruding from the head part 10 in FIG. 1, it is not limited thereto. For example, a separate groove or hole may be formed in the head part 10, and the electrode 11 may be inserted into the groove or hole. In this case, the electrode 11 may have a shape that does not protrude to the outside.

The handle part 20 is connected to the head part 10 and may have a shape that can be gripped by a user. A separate button or switch (not shown) for operating the oral care device 1 may be disposed on the handle part 20.

The signal supply part 40 is located inside the handle part 20 and may generate the driving signal Vd by using a battery voltage Vb supplied from the battery 30.

In particular, the signal supply part 40 generates the driving signal Vd by mixing an alternating current (AC) signal and a direct current (DC) signal.

Accordingly, the driving signal Vd includes both an AC component and a DC component, and a synergistic effect and resonance may occur due to the simultaneous application of the AC component and the DC component, thereby enhancing the removal effect of a biofilm that causes the dental plaque.

Referring to FIG. 2A, the electric field by the DC component may induce an imbalance in the local charge distribution to increase the structural stress of the biofilm, and the electric field by the AC component may increase the permeability of the outer shield through the generation of specific vibrations.

The synergistic effect of these AC component and DC component can be confirmed in FIG. 2B. That is, it can be seen that compared to the biofilm removal effect when the electric field from the AC component and the electric field from the DC voltage are each provided alone, the biofilm removal effect is significantly dominant when the electric field from the AC component and the electric field from the DC voltage are superimposed and provided simultaneously.

Since the electric field based on the DC component and the electric field based on the AC component may be provided simultaneously from the electrode 11 according to the driving signal Vd supplied by the signal supply part 40 according to the embodiment of the present invention, it is possible to achieve the amplified removal effect in relation to the biofilm described above.

In addition, as the driving signal Vd is set in the form of superimposing the AC voltage and the DC voltage as described above, the risk of electric shock to the body and the pain that may be caused to the body may be reduced compared to the case where only the DC voltage is applied.

Meanwhile, the battery 30 may be accommodated inside the handle part 20 and may provide the battery voltage Vb to the signal supply part 40.

For example, the battery 30 may be set as a primary battery or a secondary battery.

When the battery 30 is a primary battery, the user can periodically replace the battery 30, and when the battery 30 is a secondary battery, charging may be performed through various charging methods.

For example, the battery 30 may be charged through a wireless charging method or a wired charging method while being located in the handle part 20, or may be charged through a separate charging device separated from the handle part 20.

Figure 3:
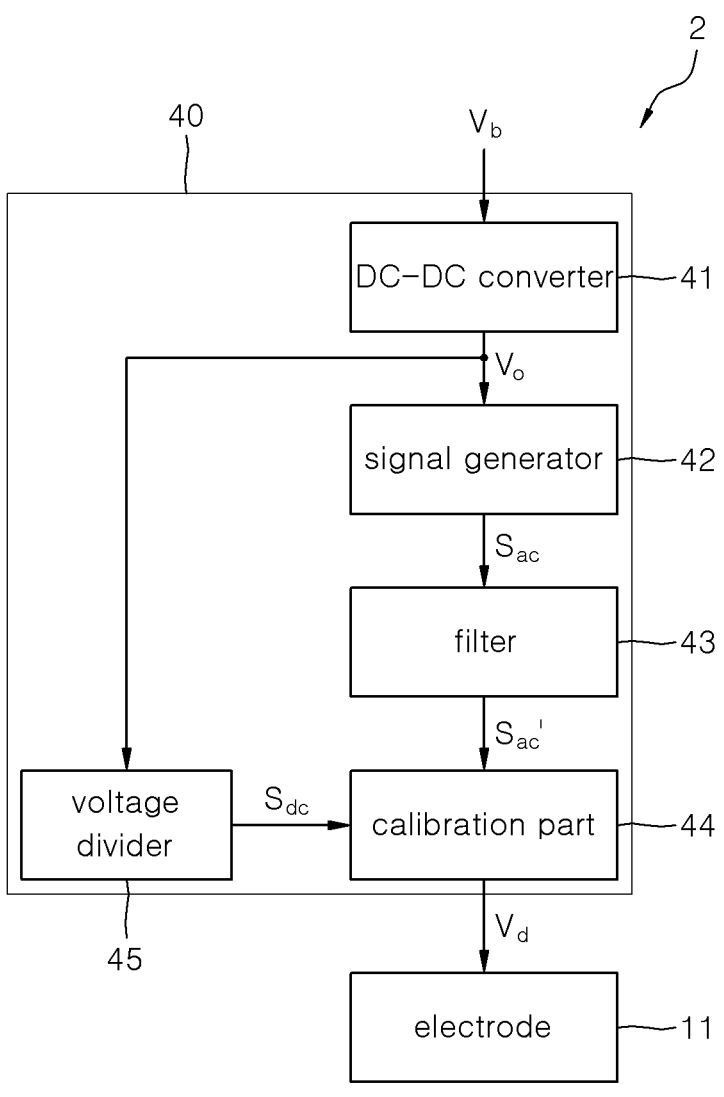
FIG. 3 is a view showing an electric field generating device for oral care according to an embodiment of the present invention.
Figure 4A:
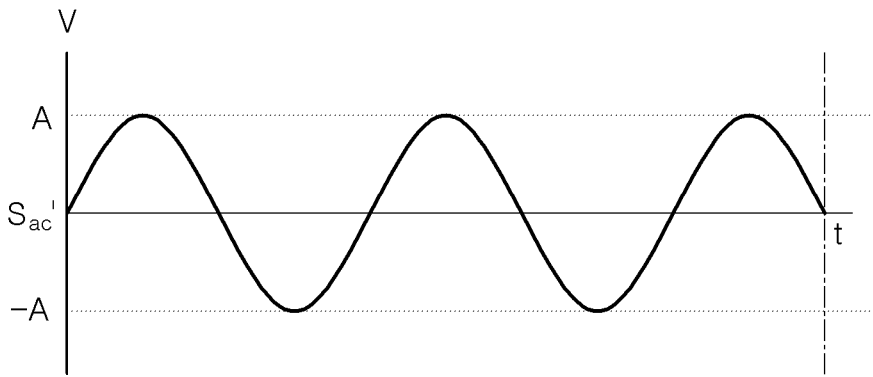
FIGS. 4A to 4C are diagrams showing waveforms of signals according to an embodiment of the present invention.
Figure 4B:
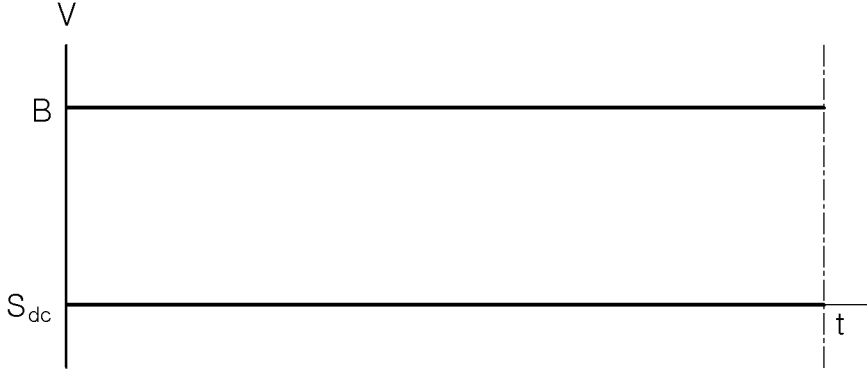
Figure 4C:
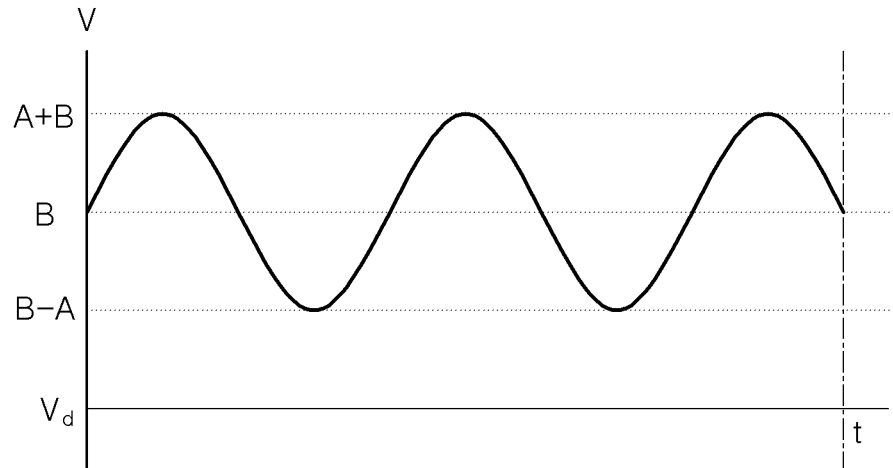

FIG. 3 is a view showing the electric field generating device for oral care according to an embodiment of the present invention, and FIGS. 4A to 4C are diagrams showing waveforms of signals according to an embodiment of the present invention. In particular, FIG. 4A shows a filtered AC signal Sac', FIG. 4B shows a DC signal Sdc, and FIG. 4C shows the driving signal Vd generated by mixing the filtered AC signal Sac' and the DC signal Sdc.

Referring to FIG. 3, the signal supply part 40 according to an embodiment of the present invention may include a DC-DC converter 41, a signal generator 42, a filter 43, and a calibration part 44, and may further include a voltage divider 45 additionally.

The DC-DC converter 41 may receive the battery voltage Vb from the battery 30, convert the battery voltage Vb into an output voltage Vo of a predetermined level, and output the converted voltage.

The signal generator 42 operates based on the voltage supplied from the DC-DC converter 41, and may generate the AC signal Sac having a predetermined frequency using the output voltage Vo of the DC-DC converter 41.

The signal generator 42 may be implemented using a previously known configuration capable of generating the AC signal such as an oscillator or a function generator.

For example, the AC signal Sac may be set to a frequency of 1 KHz to 1,000 MHz. This is because when the AC signal Sac is set to a low frequency of less than 1 KHz, the removal effect of the dental plaque is reduced, and even when the AC signal Sac is set to a very high frequency of more than 1,000 MHz, the removal effect of the dental plaque is reduced. Meanwhile, the frequency of the AC signal Sac may be set to a frequency of 5 MHz to 15 MHz suitable for removing the dental plaque.

In addition, the amplitude of the AC signal Sac may be set to 0.1 my to 3V. This is because when the amplitude of the AC signal Sac is less than 0.1 mV, it is difficult to expect the plaque removal effect, and when the amplitude of the AC signal Sac exceeds 3V, there is a concern that toxic substances may be generated due to electrolysis of body fluids.

The filter 43 may perform a filtering operation on the AC signal Sac generated by the signal generator 42. For example, the filter 43 may include a low pass filter to convert a sawtooth wave type AC signal Sac into a sine wave type AC signal Sac'. However, the type of filter 43 is not limited thereto, and various types of filters may be employed depending on the design structure.

The calibration part 44 may generate the driving signal Vd by mixing the AC signal Sac' supplied through the filter 43 with the DC signal Sdc. For example, the calibration part 44 may be implemented as an operating amplifier capable of summing (or superimposing) the AC signal Sac' and the DC signal Sdc, but is not limited thereto.

Accordingly, an offset corresponding to the DC signal Sdc may be generated in the AC signal Sac', and the driving signal Vd possessed by both the AC component and the DC component may be generated.

Since the driving signal Vd includes all the characteristics of the AC signal Sac, the driving signal Vd may be set to a frequency of 1 KHz to 1,000 MHz, and also may be set to a frequency of 5 MHz to 15 MHz more suitable for removing the dental plaque. Also, the amplitude of the driving signal Vd may be set to 0.1 my to 3V.

Referring to FIG. 4A, the calibration part 440 may receive the AC signal Sac' having an amplitude of A volt (V) from the filter 43, and the final driving signal Vd shown in FIG. 4C may be generated by superimposing the DC signal Sdc of B volt (V) as shown in FIG. 4B on the corresponding AC signal Sac'.

In this case, the voltage value of the DC signal Sdc may be set equal to or greater than the amplitude of the AC signal Sac'. Accordingly, the voltage value of the driving signal Vd may be set to 0 or more.

As a result, the DC offset value of the driving signal Vd may be set equal to or greater than the amplitude of the driving signal Vd.

Meanwhile, the DC signal Sdc may be generated by the voltage divider 45. For example, the voltage divider 45 may receive the output voltage Vo of the DC-DC converter 41 and perform voltage division on the output voltage Vo to generate the DC signal Sdc.

The voltage divider 45 may be composed of a resistance string for distributing the output voltage Vo, but is not limited thereto.

When the output voltage Vo of the DC-DC converter 41 is suitable to be used directly to generate the driving signal Vd, the corresponding output voltage Vo may serve as the DC signal Sdc. In this case, the voltage divider 45 may be omitted, and the output voltage Vo of the DC-DC converter 41 may be input to the calibration part 44.

Figure 5:
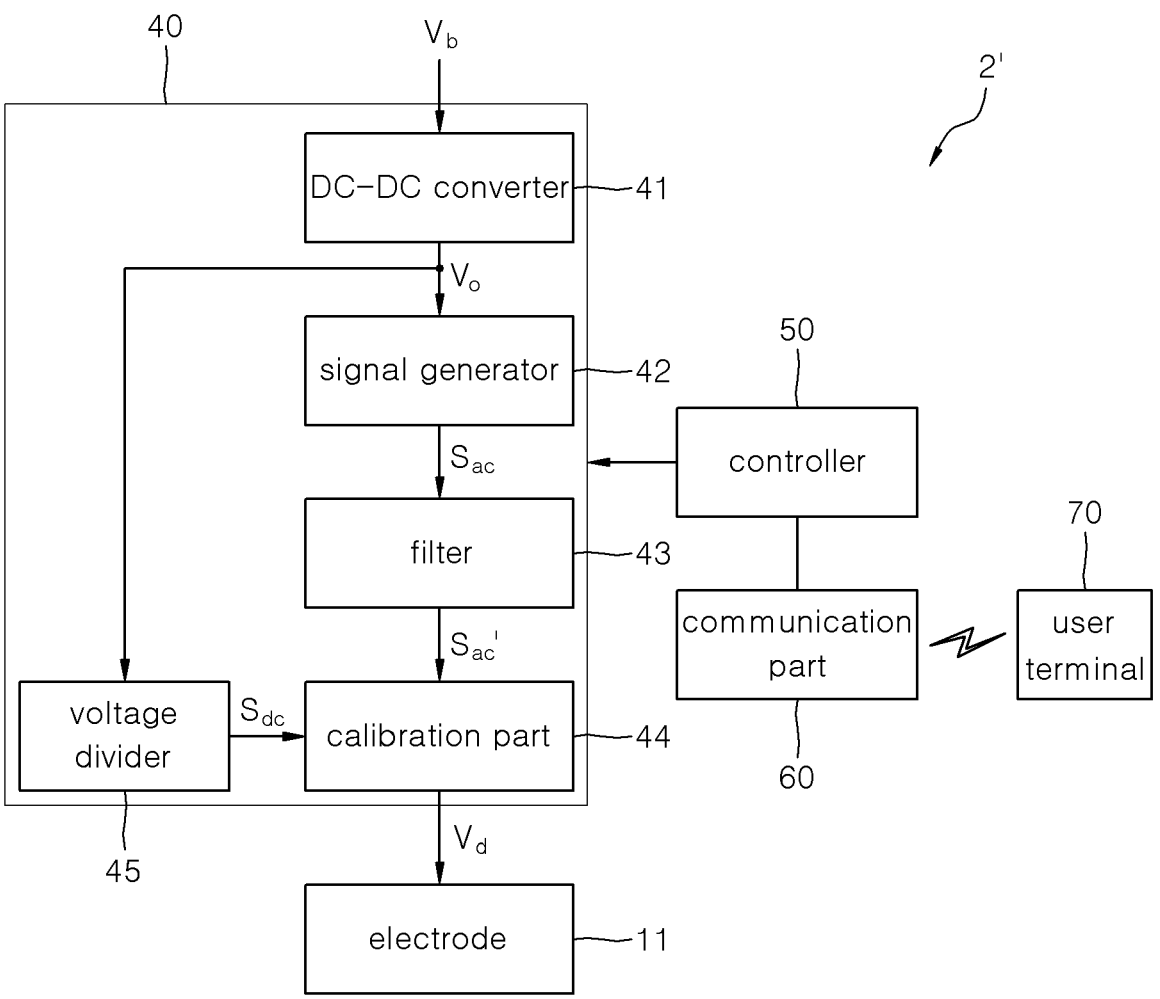
FIG. 5 is a diagram showing an electric field generating device for oral care according to another embodiment of the present invention.
Figure 6A:
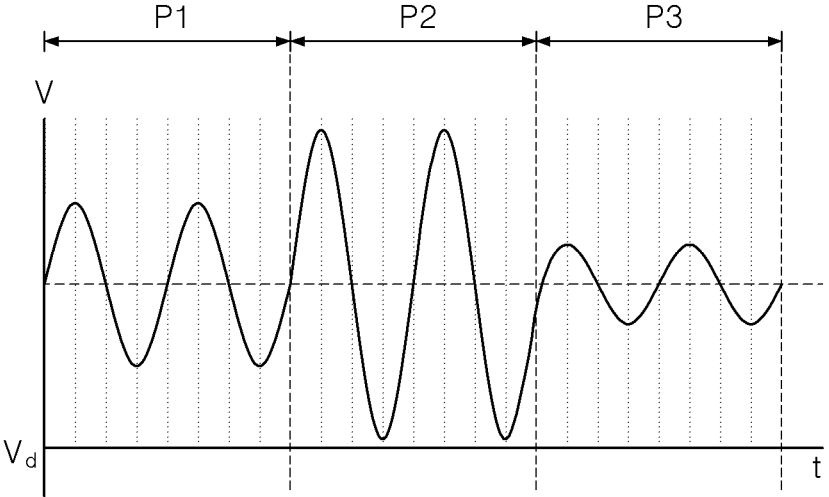
FIGS. 6A to 6C are diagrams showing how the characteristics of the driving signal are changed according to an embodiment of the present invention.
Figure 6B:
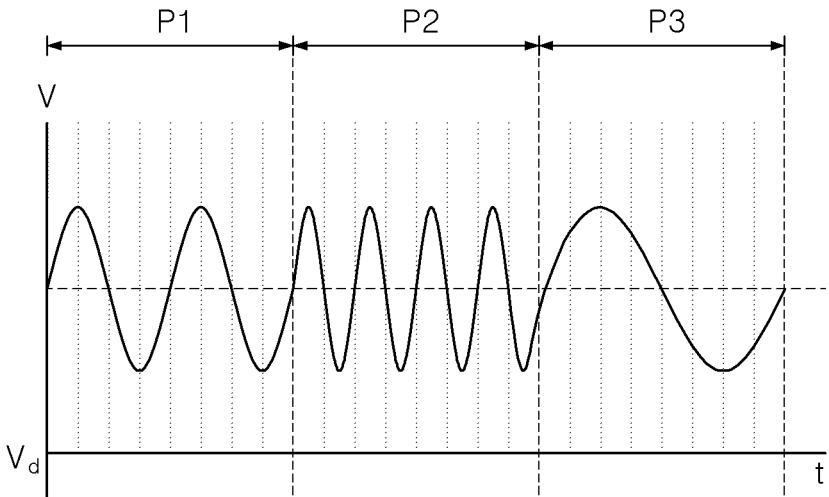
Figure 6C:
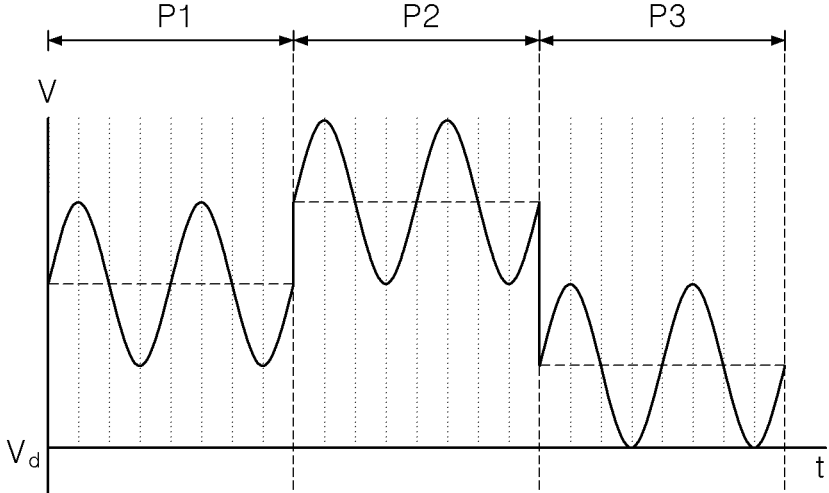

FIG. 5 is a view showing an electric field generating device for oral care according to another embodiment of the present invention, and FIGS. 6A to 6C are diagrams showing how characteristics of the driving signal are changed according to an embodiment of the present invention. In particular, FIG. 6A shows how the amplitude is changed among the characteristics of the driving signal Vd, FIG. 6B shows how the frequency changes among the characteristics of the driving signal Vd, and FIG. 6C shows how DC offset changes among the characteristics of the driving signal Vd.

Referring to FIG. 5, in an electric field generating device 2' for oral care according to another embodiment of the present invention, the signal supply part 40 may change at least one of the characteristics of the driving signal Vd in response to a user's control. In addition, the electric field generating device 2' for oral care may further comprise a controller 50 that controls the signal supply part 40 in response to a user's input.

For example, the characteristics of the driving signal Vd may include the amplitude, frequency, and DC offset of the driving signal Vd.

In other words, the user can set the optimum driving signal Vd suitable for the user by adjusting the characteristics of the driving signal Vd. This feature enables personalized oral care that takes into account individual characteristics such as gender, age, periodontal disease, etc.

In this case, the user's input method for controlling the characteristics of the driving signal Vd may be made in various ways. For example, the driving signal Vd may be adjusted by a user manipulating a button or a switch installed in the electric field generating device 2' or the oral care device 1.

In addition, the electric field generating device 2' may further include a communication part 60 capable of wireless communication with a user terminal 70, and accordingly, the user may adjust the characteristic of the driving signal Vd through his or her terminal 70.

The user terminal 70 is not particularly limited as long as it has a communication function connected to the electric field generating device 2' and a display function capable of outputting images or texts. For example, the user terminal 70 may include a desktop computer, a laptop computer, a tablet PC, a wireless phone, a mobile phone, and a smart phone, a smart watch, a smart glass, a wearable device, etc., but are not limited thereto.

In addition, the communication part 60 may be wirelessly connected to the user terminal 70 to transmit/receive data with the user terminal 70. For example, the communication part 60 may be wirelessly connected to the user terminal 70 through a short-range wireless communication method such as Bluetooth or WiFi. However, the wireless communication method of the communication part 60 is not limited thereto, and various known wireless communication methods may be employed.

The user may check current characteristic information of the driving signal Vd through the user terminal 70 wirelessly connected to the electric field generating device 2'. For example, the controller 50 may transmit current state values such as the amplitude, frequency, and DC offset of the driving signal Vd to the user terminal 70 in response to a request from the user terminal 70.

The user can change the characteristics of the driving signal Vd when necessary by referring to the characteristic information of the driving signal Vd.

That is, a user who needs to change the characteristics of the driving signal Vd can transmit setting information for changing the characteristics of the driving signal Vd to the electric field generating device 2' using the user terminal 70.

For example, the setting information may include at least one of the user's gender, age, and periodontal disease possession information.

The controller 50 may determine the characteristics of the driving signal Vd suitable for the user by referring to the user's gender, age, and periodontal disease possession information, transmitted from the user terminal 70. For example, the controller 50 may utilize a separate table or data in which setting information such as the user's gender, age, periodontal disease possession information, etc., and corresponding characteristic information of the driving signal Vd are stored.

When the characteristic value of the driving signal Vd corresponding to the setting information input by the user is determined, the controller 50 may control the signal supply part 40 so that the driving signal Vd has the determined characteristic value.

Meanwhile, the user may perform characteristic control of the driving signal Vd by directly inputting a characteristic value of the driving signal Vd which the user desires.

In this case, the setting information provided from the user terminal 70 may include at least one of an amplitude setting value, a frequency setting value, and a DC offset setting value.

In response to this setting information, the controller 50 may control the signal supply part 40 so that the driving signal Vd has a characteristic value corresponding to the setting information (or the setting value).

The controller 50 may change the amplitude and/or frequency of the AC signal Sac by controlling the signal generator 42. Also, the controller 50 may adjust the voltage value of the DC signal Sdc by controlling the DC-DC converter 41 and/or the voltage divider 45. Accordingly, the characteristics of the driving signal Vd may be finally changed.

Referring to FIG. 6A, the signal supply part 40 may change the amplitude of the driving signal Vd, and referring to FIG. 6B, the signal supply part 40 may change the frequency of the driving signal Vd. Also, referring to FIG. 6C, the signal supply part 40 may change the DC offset of the driving signal Vd.

FIGS. 6A, 6B, and 6C show how only one of the characteristics of the driving signal Vd is changed, but this is an example and it goes without saying that many of the characteristics of the driving signal Vd may be changed in combination.

In addition, the signal supply part 40 may automatically change at least one of the characteristics of the driving signal Vd for each unit time P1, P2, and P3 during a predetermined period.

For example, the user can determine a use mode suitable for the user and set the corresponding use mode through the above described input method. In this case, the controller 50 may automatically change the characteristics of the driving signal Vd over time in response to the set use mode.

As shown in FIG. 6A, the amplitude characteristic of the driving signal Vd may be automatically changed for each unit time P1, P2 and P3 for a predetermined period, and as shown in FIG. 6B, the frequency characteristics of the driving signal Vd may be automatically changed for each unit time P1, P2 and P3 during a preset period. In addition, as shown in FIG. 6C, the DC offset characteristics of the driving signal Vd may be automatically changed for each unit time P1, P2 and P3 during a preset period.

As described above, even in this automatic change mode, many of the characteristics of the driving signal Vd may be complexly changed.

Those skilled in the art to which the present invention pertains will understand that the present invention can be embodied in other specific forms without changing its subject matter or essential features. Therefore, it should be understood that the embodiments described above are illustrative only and not restrictive. The scope of the present invention is defined by the claims below rather than the detailed description above, and all changes or modifications derived from the claims and their equivalents should be construed as being included in the scope of the present invention.

The invention claimed is:

1. An electric field generating device for oral care, comprising:
   at least one electrode configured to receive a driving signal and generate an electric field corresponding to the driving signal; and
   a signal supply part configured to generate the driving signal by mixing an alternating current (AC) signal and a direct current (DC) signal and supply the driving signal to the at least one electrode, wherein the signal supply part includes:

a DC-DC converter configured to receive a battery voltage and convert the battery voltage into an output voltage;

a signal generator configured to generate the AC signal using the output voltage of the DC-DC converter;

a filter configured to perform a filtering operation on the AC signal generated by the signal generator; and a calibration part, including an amplifier, configured to generate the driving signal by mixing the DC signal with the AC signal supplied through the filter.

2. The electric field generating device for oral care according to claim 1, wherein the signal supply part changes at least one of characteristics of the driving signal in response to a user's control.

3. The electric field generating device for oral care according to claim 2, wherein the characteristics of the driving signal include an amplitude, a frequency, and a DC offset.

4. The electric field generating device for oral care according to claim 2, further comprising a user's terminal;

a communication part, including Bluetooth or WiFi transceiver, configured to wirelessly communicate with the user's terminal; and a controller configured to transmit current characteristic information of the driving signal to the user's terminal through the communication part.

5. The electric field generating device for oral care according to claim 4, wherein the signal supply part changes at least one of the characteristics of the driving signal in response to setting information transmitted from the user's terminal through the communication part.

6. The electric field generating device for oral care according to claim 5, wherein the setting information includes at least one of the user's gender, age, and periodontal disease possession information.

7. The electric field generating device for oral care according to claim 5, wherein the setting information includes at least one of an amplitude setting value, a frequency setting value, and a DC offset setting value.

8. The electric field generating device for oral care according to claim 2, wherein the signal supply part automatically changes at least one of the characteristics of the driving signal for each unit time during a predetermined period of time.

9. The electric field generating device for oral care according to claim 1, wherein the signal supply part further includes a voltage divider configured to generate the DC signal by dividing the output voltage of the DC-DC converter.

10. The electric field generating device for oral care according to claim 1, wherein the calibration part includes an operational amplifier.

11. The electric field generating device for oral care according to claim 1, wherein a frequency of the driving signal is 1 kHz to 1,000 MHz.

12. The electric field generating device for oral care according to claim 1, wherein an amplitude of the driving signal is 0.1 mV to 3 V.

13. The electric field generating device for oral care according to claim 12, wherein a voltage value of the DC signal is set equal to or greater than a amplitude of the AC signal.

* * * * *